US006396931B1

(12) United States Patent
Malilay

(10) Patent No.: US 6,396,931 B1
(45) Date of Patent: May 28, 2002

(54) ELECTRONIC STETHOSCOPE WITH DIAGNOSTIC CAPABILITY

(76) Inventor: Cicero H. Malilay, 3586 S. Sepulveda Blvd. #7, Los Angeles, CA (US) 90034

( * ) Notice: Subject to any disclaimer, the term of this patent is extended or adjusted under 35 U.S.C. 154(b) by 0 days.

(21) Appl. No.: 09/265,239

(22) Filed: Mar. 8, 1999

(51) Int. Cl.[7] .............................. A61B 7/04; A61B 7/02

(52) U.S. Cl. .......................................... 381/67; 181/131

(58) Field of Search ............................ 381/67; 181/126, 181/131; 600/510, 522, 523; 73/591

(56) References Cited

U.S. PATENT DOCUMENTS 4,770,189 A * 9/1988 Shyu .......................... 381/67
5,025,809 A * 6/1991 Johnson et al. ............. 128/715
5,185,803 A * 2/1993 Moyski et al. ................ 381/92
5,218,969 A * 6/1993 Bredesen et al. ............. 381/67
5,360,005 A * 11/1994 Wilk ....................... 128/653.1
5,557,681 A * 9/1996 Thomasson .................. 381/67

* cited by examiner

*Primary Examiner*—Forester W. Isen
*Assistant Examiner*—Laura A. Grier
(74) *Attorney, Agent, or Firm*—A. M. Fernandez

(57) ABSTRACT

A self-contained, hand-held electronic stethoscope including built-in chestpiece, speaker and visual monitor, includes a memory containing prerecorded heart and lung sounds along with a brief description of the malady producing the sounds so that the technician may compare the actual sounds with the prerecorded sounds and observe a suggested diagnosis on the monitor.

4 Claims, 1 Drawing Sheet

40
28
32
36
34
14
46
46
46
46

ELECTRONIC STETHOSCOPE WITH DIAGNOSTIC CAPABILITY

This invention relates to electronic stethoscopes and in particular to a stethoscope in which the output may be compared both by sound and visually on a scope with various sound signals prerecorded on a memory medium.

BACKGROUND OF THE INVENTION

Various pathological conditions of a patient are revealed by auscultation examination. A normal heart and lungs produce normal sounds which are detected by the stethoscope, and if any abnormalities are detected proper corrective steps may be taken Therefore, it is extremely important for a medical diagnostician to recognize and understand normal and abnormal heart and lung sounds.

There are many heart sounds that must be learned by the diagnostician. The human heart has four chambers. During the diastolic or relaxed period, blood flows through the tricuspid valve into the right ventricle and oxygenized blood flows through the mitral valve into the left ventricle. At the end of this very short diastolic period the mitral valve closes followed by the tricuspid valve and the heart muscle contracts in systole while blood is pumped from the right ventricle through the pulmonary valve and blood is pumped from the left ventricle through the aortic valve. There is a sound, called S1, that occurs at the closure of the mitral and tricuspid valves and a sound, S2, that occurs at the closure of the aortic and pulmonary valves.

With the presence of heart disease the individual sounds are often split and may be heard as two sounds on each of the two basic S1 and S2 sounds. And in addition to the basic sounds, there are pathologic sounds which may be caused by blood passing through a tight valve or a pathologically enlarged valve opening. And certain disease processes may cause rubbing sounds produced by rubbing of the heart wall on the tissue covering that surrounds the heart. Certain diseases can change or vary the heart sounds. For example, if S1 appears to be louder than S2, it suggests a tightening of the mitral valve or mitral stenosis, whereas an unusually soft S2 suggests mitral regurgitation. Heart disease is suggested if any component separation occurs during expiration, if separation seems excessive, or if one component is persistently missing.

Lung sounds also have two components, that produced by inspiration and that by expiration. With a presence of disease in the lungs the normal lung sounds are disrupted and certain pathologic crackles, rates and wheeze sounds are produced which, in most instances, would point to a certain disease going on in the patient's pulmonary and even systemic system.

The foregoing material discusses only a small fraction of the various sounds that may be detected with a stethoscope. There is a multitude of murmurs, hums and clicks that may be heard at various body locations while in various positions. It is thus apparent that the science of auscultation is difficult and that certain medical technicians, such as ambulance technicians or student who may not have thoroughly mastered the science, would benefit greatly from a stethoscope that included a diagnostic capability.

Briefly described, this invention is for a self-contained electronic stethoscope in a housing that includes a prerecorded record of typical sounds, a recorded image of the external pulse recordings of the sound and a suggested diagnosis. The electronic stethoscope normally outputs into a small speaker and to a small oscilloscope for viewing the signal, and depressing a momentary contact switch will divert the prerecorded record output to the speaker and scope for comparison with the stethoscope sounds

DESCRIPTION OF THE DRAWINGS

In the drawings which illustrate the preferred embodiment of the invention.

DETAILED DESCRIPTION OF THE PREFERRED EMBODIMENT

The invention is for an electronic stethoscope that has the capability of diagnosing physical problems by providing a means for comparing a stethoscope sound and oscilloscope image with a typical sound and identified image that has been prerecorded on a magnetic memory disc within the hand held stethoscope housing containing amplifying circuitry, the prerecorded memory and a battery for supplying power.

Figure 1:
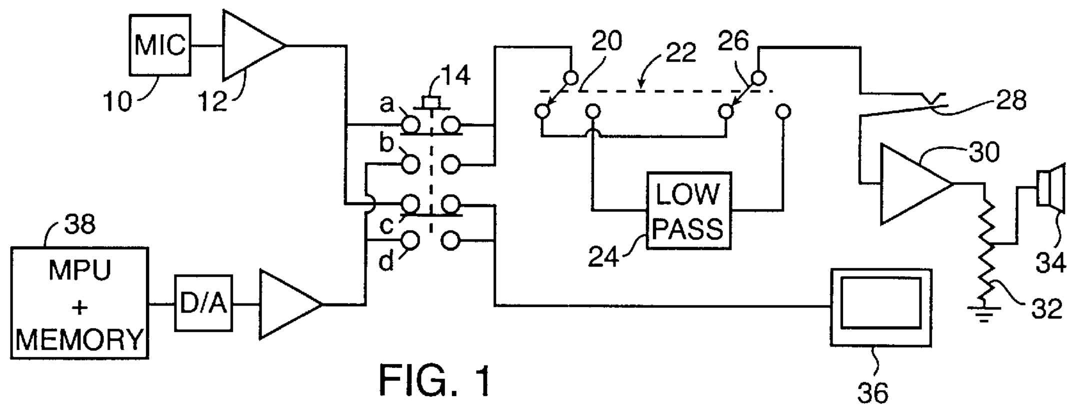
FIG. 1 is a schematic drawing of the electronic stethoscope with diagnostic capability.

The self-contained circuitry of the stethoscope is illustrated in FIG. 1 and comprises a microphone 10 located in the stethoscope chest piece, immediately followed by wide band low power amplifier 12 the output of which is applied to the switch 14. Switch 14 preferably is comprised of four ganged, single-pole, single-throw switches which are connected into a spring loaded, momentary contact, single double-pole, double-throw configuration so that, in its normal state, one pole couples the amplifier 12 to a speaker for a sound output and the second pole couples the amplifier 12 to a monitor for a visual output of the waveform. When depressed, the first pole of switch 14 couples a prerecorded sound to the speaker and the second pole couples it to the monitor.

Thus, the output of amplifier 12 is coupled to terminal "a" of the switch 14 and normally passes to pole 16 of the switch. Pole 16 of switch 14 is connected to pole 20 of a double-pole double-throw switch 22 which, in a first position passes the signal from amplifier 12 to a second amplifier and a speaker and, in the second position, diverts the signal to the amplifier and speaker through a low pass filter 24 which may be switched on to eliminate all high frequency sounds above approximately 500 Hertz.

The output of the switch 22 is taken from the second pole 26 and after passing through a "privacy" phone jack 28, is applied to the second or power amplifier 30, the output of which is applied through a volume control 32, having an "ON-OFF" power switch, to a speaker 34. The output of amplifier 12 is also coupled to terminal "c" of the switch 14 and normally passes to pole 18 of the switch which is connected to the "X" or vertical deflection input on a small monitor 36 having, for example, a one or two inch oscilloscope tube.

Various heart and lung sounds are prerecorded along with a very short diagnosis of the defect causing the sound. All the heart and lung sounds and the associated suggested diagnoses are recorded on a miniature diskette which can be easily accommodated with the associated circuitry within the hand-held housing of the stethoscope. The approximate sector of the expected recorded sound on the diskette is selected by depressing a button on the housing and the recording may be "inched" forward and backward to find the desired location by an "up" or "down" sliding of the button of the spring biased switch 14 on the side of the housing.

The miniature memory diskette is contained in the memory and microprocessor, the output of which is converted into analog and applied to input terminals "b" and "d" of the switch 14 so that, when switch is momentarily depressed, the prerecorded signals are applied to the speaker 34 and to the monitor 36.

Figure 2:
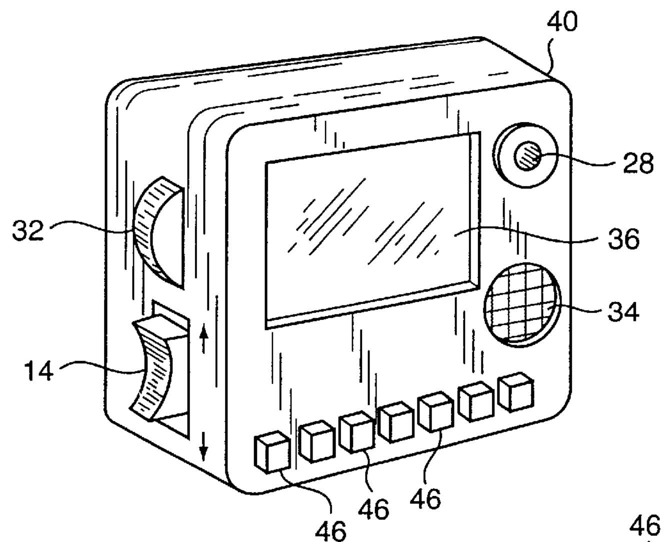
FIG. 2 is a perspective view of the stethoscope housing.
Figure 3:
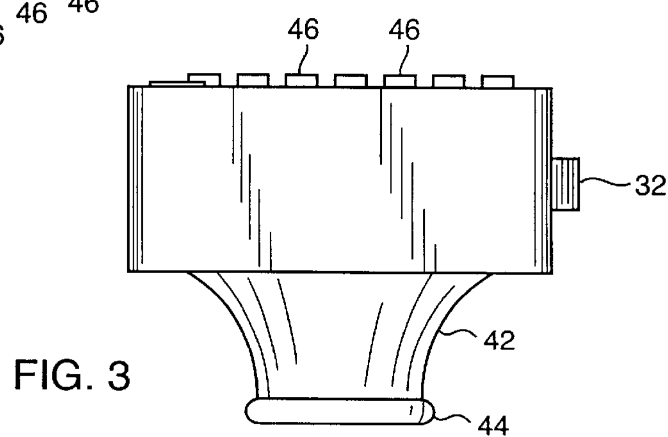
FIG. 3 is a top plan view thereof.

FIG. 2 is a perspective view illustrating one end surface and the rear surface of the stethoscope that contains the selection controls and the audio and visual outputs and FIG. 3 is a top plan view illustrating the chestpiece on the stethoscope.

The stethoscope is contained in a hand-held size housing 40 approximately three inches square and one inch thick. Centered on one of the square surfaces is a funnel shaped chestpiece 42 about two inches long and containing a very thin diaphragm near its narrow end that is backed by the microphone 10 (not shown). A rubber ring 44 is stretched over the rim of the chestpiece to assure a tight seal to the skin of a patient.

On one side of the housing 40 are two controls: The volume control 32 which regulates the audio volume, and the switch 14 which is depressed to momentarily switch on the prerecorded sound from the memory 38 and which also may slide up and down for making forward and backward adjustments in the memory location.

The square surface opposite the chestpiece 42 contains the phone jack 28, the small speaker 34, and the monitor 36 which may have a two-inch or three-inch oscilloscope tube Also on this surface are seven buttons 46, one of which is the low pass filter switch 22, and the remaining six are for selecting the various pre-recorded subjects on the disk in the memory 38. For example, the six buttons may be labeled Pulmonary Valve, Aortic Valve, Tricuspid Valve, Mitral Valve, Lungs, Blood Vessels. If Blood Vessels button has been depressed the switch button 14 may be moved so that Carotid Artery is displayed on the monitor.

In use, the stethoscope is turned ON with the power switch on the volume control 32 and the chestpiece is pressed at the appropriate body locations of a patient. The sounds picked up by the microphone 10 may be heard by earphones plugged into the phone jack 28 or they may be amplified by amplifier 30 and heard through speaker 34 while a visual representation of the sounds are seen by the monitor 36. If the technician suspects any disorders, he may press the appropriate button 46 and adjust the sliding switch 14 to the location at which matching sounds are heard on the earphones or speaker and seen on the monitor from the prerecorded diskette. For each prerecorded sound visual, there is a brief message suggesting the problem; for example, the technician may have found coincidence between a patient's sound with a pre-recorded sound labeled "Mitral Regurgitation" indicating that the patient's examination showed a probability of a weak mitral valve and having a backward flow of blood through the valve into the left atrium.

I claim:

1. An electronic stethoscope with diagnostic capability comprising:

a housing capable of being held in one hand, said housing having at least one side surface between two opposing surfaces;

a chestpiece extending from a first surface of said housing, said chestpiece containing a microphone;

a first amplifier within said housing and coupled to said microphone;

a monitor and a second amplifier with a speaker within said housing and coupled to said first amplifier, said monitor for visually displaying the sounds from said first amplifier;

a memory within said housing, said memory containing a recording of pre-recorded heart and lung sounds, each sound in said memory accompanied by a brief description of a malady suggested by the sound; and a spring-loaded, double-pole, double-throw switch attached to the side surface within said housing, said switch connected to normally pass the sounds from said microphone to said speaker and said monitor, and whereas depressing a button on said switch disconnects the sounds from said microphone and substitutes the prerecorded sounds from said memory;

a phone jack in the circuit between said spring-loaded, double-pole, double-throw switch and said second amplifier;

a low pass filter, said filter selectively activated by a second double-pole, double-throw switch in the circuit between said spring-loaded, double-pole, double-throw switch and said phone jack.

2. The electronic stethoscope claimed in claim 1 including means on an exterior surface of said housing for accessing sections of said memory to be selected.

3. The electronic stethoscope claimed in claim 2 wherein said means for accessing comprise a plurality of buttons on the surface with the monitor display, one of said buttons controlling said second double-pole, double-throw switch.

4. The electronic stethoscope claimed in claim 1 wherein the sliding of the button on said spring-loaded, double-throw, double-pole switch controls minor adjustments to the selection of said memory.

* * * * *